United States Patent [19]

Yarm

[11] Patent Number: 4,864,863
[45] Date of Patent: Sep. 12, 1989

[54] MECHANISM FOR TESTING HELICOPTER ROTOR BLADE FATIGUE PROPERTIES

[75] Inventor: Jay M. Yarm, Milford, Conn.

[73] Assignee: United Technologies Corporation, Hartford, Conn.

[21] Appl. No.: 184,919

[22] Filed: Apr. 22, 1988

[51] Int. Cl.[4] .............................................. G01N 3/34
[52] U.S. Cl. ........................................ 73/794; 73/812
[58] Field of Search ................. 73/794, 795, 796, 797, 73/798, 812, 849, 850, 851, 852, 853, 854, 808, 810

[56] References Cited

U.S. PATENT DOCUMENTS 3,170,321  2/1965  Sullivan et al. ..................... 73/812
4,089,211  5/1978  Vercellone et al. .................. 73/93

Primary Examiner—Jerry W. Myracle
Attorney, Agent, or Firm—Russell M. Lipes, Jr.

[57] ABSTRACT

Mechanism for determining the fatigue properties of helicopter rotor blade flexbeam sections using one motor driven eccentric for imparting combined bending, twisting and deflection loads to a flexbeam.

4 Claims, 2 Drawing Sheets

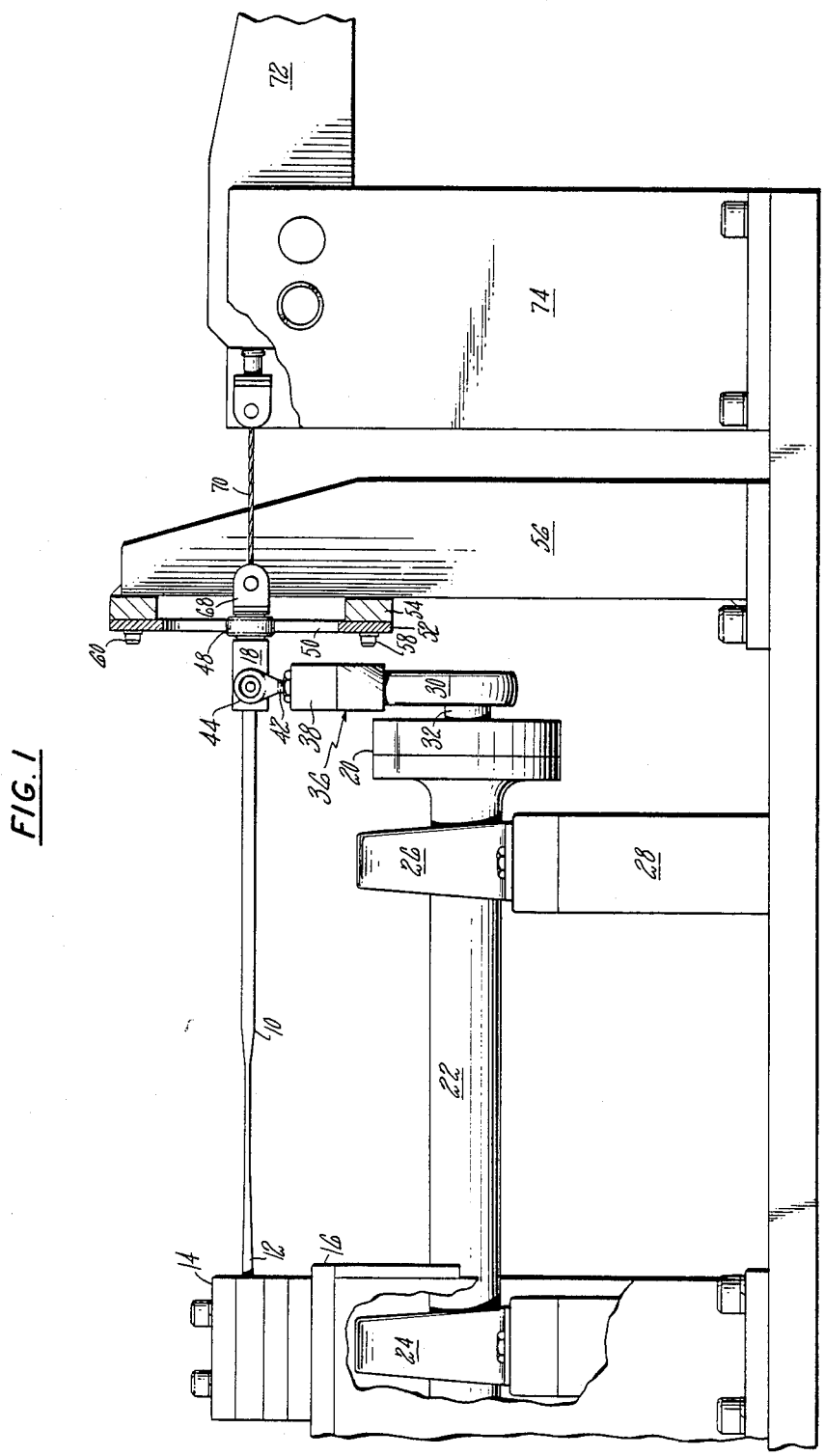

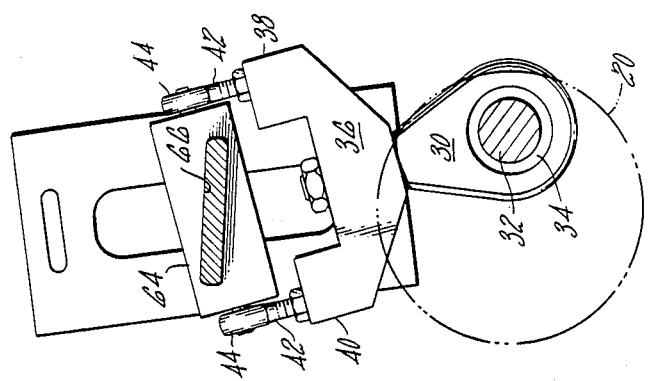
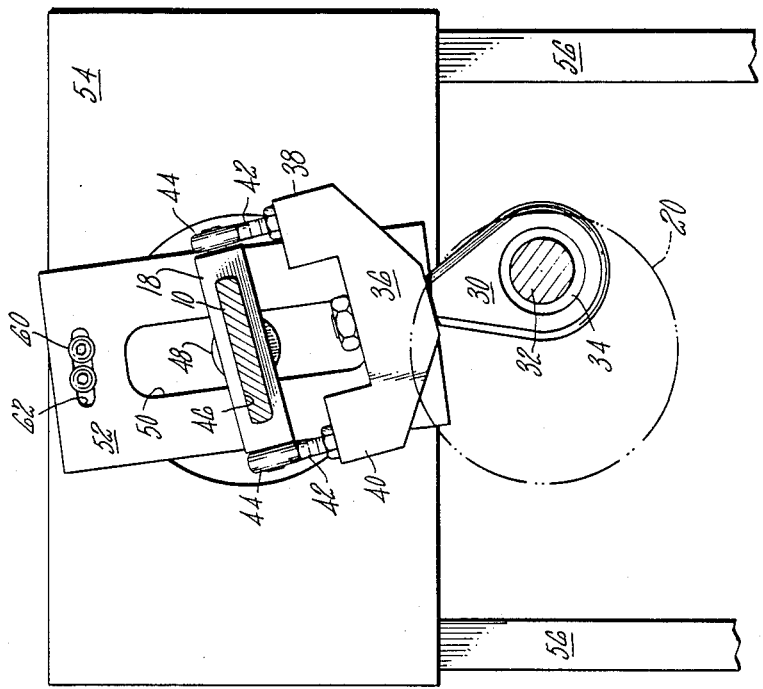

MECHANISM FOR TESTING HELICOPTER ROTOR BLADE FATIGUE PROPERTIES

DESCRIPTION

1. Technical Field

This invention relates to rotor blades for helicopters and more particularly to mechanism for determining the fatigue properties of rotor blade flexbeam sections.

2. Background Art

Fatigue testing mechanism currently in use in the helicopter industry makes extensive use of individual motor driven cranks and eccentrics or electrically controlled servo cylinders for each mode of flexbeam excitation. Separate actuators are combined in various ways for flexbeams flapwise, edgewise and twist motion inputs. The mechanism can be relatively complicated and set-up and testing can involve a greater amount of time than a unitary mechanism.

DISCLOSURE OF INVENTION

An object of the present invention is to provide a simplified rotor blade flexbeam fatigue mechanism using one motor driven eccentric to provide all motions and dynamic loadings.

Another object of the invention is to provide rotor blade flexbeam fatigue mechanism which is useful for testing resonate flapwise/edgewise frequencies since maximum flapwise displacement occurs coincidentally with maximum edgewise displacement.

The foregoing and other objects, features and advantages will be apparent from the specification and claims and from the accompanying drawings which illustrate an embodiment of the invention.

BRIEF DESCRIPTION OF THE DRAWINGS

FIG. 1 is a side view of fatigue testing mechanism constructed in accordance with this invention.

FIG. 2 is a section view of a portion of the fatigue testing mechanism of FIG. 1 showing the connection of the flexbeam to the eccentric numbers.

FIG. 3 is a section view similar to FIG. 2 but showing a set-up for testing a twisted flexbeam

BEST MODE FOR CARRYING OUT THE INVENTION

In the mechanism shown in FIG. 1, rotor flexbeam 10 is shown having its inboard or root end 12 restrained by clamp assembly 14 to mechanism base 16. The outboard tip end of the flexbeam is supported by fitting block 18 attached to eccentric plate 20 and drive shaft 22 as will be explained. The drive shaft is journally supported by bearing 24 in mechanism base 16 and bearing 26 in mechanism base member 28. The drive shaft turns eccentric rod 30 by means of pin 32 and semi-spherical ball bearing race 34, FIG. 2, which provides for small angular displacement to accommodate radial fore-shortening effects as the flexbeam moves in a bending or flapwise direction.

Rod 30 terminates in yoke 36 having arms 38 and 40. Each arm has pin 42 extending therefrom and each pin is rotatably connected by bearing 44 to fitting block 18 so that the fitting block can pivot about its longitudinal axis as flapping motion is imparted to flexbeam 10. The fitting block has slot 46 for receiving the outboard end of flexbeam 10. As shown in FIG. 2, the longitudinal axis of slot 46 is coincident with the longitudinal axis of fitting block 18. The eccentric and yoke lengths can be made adjustable to provide any required combination of flexbeam bending (flapping) and twist (pitch). The sine of the twist angle is equal to the eccentric throw divided by the yoke length. Normally, the height of mechanism base 16 is such that at the three o'clock and nine o'clock positions of the eccentric, the spanwise axis of flexbeam 10 is straight. Raising the height can provide for flapping tests about a predetermine base droop angle of the flexbeam, and lowering the height can provide for flapping tests about a predetermined base cone angle of the flexbeam.

Edgewise force and/or deflection of flexbeam 10 is controlled by cam follower 48 running in slot 50 in guide plate 52. The cam follower is attached to fitting block 18. Guide plate 52 is attached to base plate 54 and mechanism base number 56 by bolt 58 at its lower end (FIG. 1) and by bolts 60 at its top end. Slot 62 in guide plate 52, through which bolt 60 extends, permits rotation of the plate about lower end bolt 58 and thus the vertical alignment of slot 50 to be varied.

By virtue of this construction, the mechanism can be configured for any desired loading pattern. In FIG. 2, the set-up is for maximum edgewise deflection at maximum flapping angle. Cam follower bearing 48 would be in the upper portion of slot 50 and the flexbeam would be deflected to the left when eccentric rod 30 is in a top 0° position, a position of maximum upward flapping of the flexbeam. Similarly, cam follower bearing 48 would be in the lower portion of slot 50 and the flexbeam would be deflected to the right when eccentric rod 30 is in the bottom 180° position, a position of maximum downward flapping of the flexbeam. There would be no twisting of the flexbeam when eccentric rod 30 is in the 0°, or 180° positions since the axis of fitting block slot 46 would be horizontal at those two positions. Maximum twist of the flexbeam occurs in the FIG. 2 set-up when eccentric rod 30 is in the 90° and 270° positions. In those positions, there is no edgewise deflection or flapping input into the flexbeam. Slot 50 need not be configured as straight, but may be curved so as to provide other combinations of edgewise loading and phasing.

FIG. 3 illustrates a test set-up of a flexbeam having a built-in twist. In this set-up, fitting block 64 has slot 66, the lengthwise axis of which is at an angle to the rotational axis of the fitting block rather than being parallel to it as in FIG. 2. Testing of the blade, that is, flapping, deflecting and twisting, would be conducted about the built-in twist with the built-in twist angle serving as the base parameter.

As shown in FIG. 1, provision is made for imposing centrifugal loading on the flexbeam. Lug 68 is attached to the end of flexbeam 10 and is connected by cable 70 to weight table bellcrank 72 rotatably connected to base 74. Through the bellcrank, various steady centrifugal loads can be imposed upon the flexbeam.

It should be understood that the invention is not limited to the particular embodiments shown and described, but that various changes and modifications may be made without departing from the spirit or scope of this concept as defined by the following claims.

I claim:

1. Mechanism to produce combined loadings in and out of phase on a helicopter rotor blade flexbeam, said mechanism including means for restraining the root end of a flexbeam and means for imparting bending, twisting and deflection loading on the opposite tip end of said flexbeam, said loading imparting means including motor means driving eccentric means, yoke means connected to said eccentric means and the tip end of said flexbeam for controlled bending and twisting of said flexbeam upon operation of said motor means, and cam means for controlling deflection of said flexbeam upon operation of said motor means.

2. Mechanism to produce combined loadings in and out of phase on a helicopter rotor blade flexbeam, said mechanism including means for restraining the root end of a flexbeam and means for imparting bending, twisting and deflection loading on the opposite tip end of said flexbeam, said loading imparting means including motor means driving eccentric means, having an adjustable length eccentric arm, adjustable length yoke means connected to said eccentric arm and the tip end of said flexbeam, said yoke means including first means having slot means for receiving said flexbeam tip end, said first means being rotatable about its longitudinal axis as bending motion is imparted to said flexbeam, said slot means having a longitudinal axis the angle of which relates to the longitudinal axis of said first means in accordance with blade twist, cam follower means integral with said first means, and guide means for receiving said cam follower so as to impart deflection to said flexbeam.

3. Mechanism to produce combined loadings in and out of phase on a helicopter rotor blade flexbeam, said mechanism including means for restraining the root end of a flexbeam and means for imparting bending, twisting and deflection loading on the opposite tip end of said flexbeam, said loading imparting means including motor means driving eccentric means, having an adjustable length eccentric arm, adjustable length yoke means connected to said eccentric arm and the tip end of said flexbeam, said yoke means including a fitting block having a slot adapted to receive the tip end of said flexbeam and having a rotating connection with said yoke means, cam follower means integral with said fitting block, guide means for said cam follower means, and means for adjusting the position of said guide means to vary flexbeam deflection during testing.

4. Mechanism to produce combined loadings in and out of phase on a helicopter rotor blade flexbeam, said mechanism including means for restraining the root end of a flexbeam and means for imparting bending, twisting and deflection loading on the opposite tip end of said flexbeam, said loading imparting means including motor means driving eccentric means, having an adjustable length eccentric arm, adjustable length yoke means connected to said eccentric arm and the tip end of said flexbeam, said yoke means including first means having slot means for receiving said flexbeam tip end, said first means being rotatable about its longitudinal axis as bending motion is imparted to said flexbeam, said slot means having a longitudinal axis the angle of which relates to the longitudinal axis of said first means in accordance with blade twist, cam follower means integral with said first means, and guide means for receiving said cam follower so as to impart deflection to said flexbeam and means connected to the tip end of said flexbeam to apply centrifugal loading during testing.

* * * * *